United States Patent
Miller et al.

[11] Patent Number: 5,875,968
[45] Date of Patent: Mar. 2, 1999

[54] LIQUID AIR FRESHENER DISPENSER DEVICE WITH NONPOROUS CAPILLARY WICKING FUNCTION

[75] Inventors: Eric J. Miller, Mount Pleasant; John Martin, Caledonia, both of Wis.

[73] Assignee: S. C. Johnson & Son, Inc., Racine, Wis.

[21] Appl. No.: 896,666

[22] Filed: Jul. 18, 1997

[51] Int. Cl.⁶ .................................................. A24F 25/00
[52] U.S. Cl. .............................................. 239/44; 239/34
[58] Field of Search .................................. 239/34, 43, 44, 239/47, 49, 50

[56] References Cited

U.S. PATENT DOCUMENTS

| | | |
|---|---|---|
| 1,994,932 | 3/1935 | Vidal . |
| 2,597,195 | 5/1952 | Smith . |
| 2,802,695 | 8/1957 | Johnson . |
| 2,804,291 | 8/1957 | Hard AF Segerstad . |
| 2,847,976 | 8/1958 | Spaulding . |
| 3,283,787 | 11/1966 | Davis . |
| 3,550,853 | 12/1970 | Gray . |
| 3,727,840 | 4/1973 | Nigro ........................................ 239/43 |
| 4,286,754 | 9/1981 | Jones . |
| 4,314,915 | 2/1982 | Wiegers . |
| 4,411,829 | 10/1983 | Schulte-Elte et al. . |
| 4,413,779 | 11/1983 | Santini . |
| 4,434,306 | 2/1984 | Kobayashi et al. . |
| 4,454,987 | 6/1984 | Mitchell . |
| 4,913,349 | 4/1990 | Locko ....................................... 239/34 |
| 4,913,350 | 4/1990 | Purzycki . |
| 5,000,383 | 3/1991 | van der Heijden . |
| 5,121,881 | 6/1992 | Lembeck .................................. 239/44 |
| 5,749,519 | 5/1998 | Miller ....................................... 239/44 |
| 5,749,520 | 5/1998 | Martin et al. ............................. 239/44 |

*Primary Examiner*—Andres Kashnikow
*Assistant Examiner*—Dinh Q. Nguyen
*Attorney, Agent, or Firm*—J. William Frank, III

[57] ABSTRACT

This invention provides an air freshener dispenser device with a nonporous wicking feature, which consists of (a) a first container with an upside open end, and a downside closed end with a sharp piercing structure extending up from the interior bottom surface, (b) a second container which is inverted and internally-nested within the first container, with an upside closed end comprising a vapor-emanating means, and a downside end which is sealed with an impermeable membrane, and (c) a reservoir of liquid air freshener medium enclosed within the second container. The coextensive sidewalls of the two containers are in a capillary spacing proximity. For activation of the dispenser device into an operational mode, the second container is adjusted until the impermeable membrane is breached by the sharp-structure at the bottom of the first container. The released air freshener medium is transported by capillary action to the vapor-emanating surface for evaporation into the atmosphere.

10 Claims, 2 Drawing Sheets

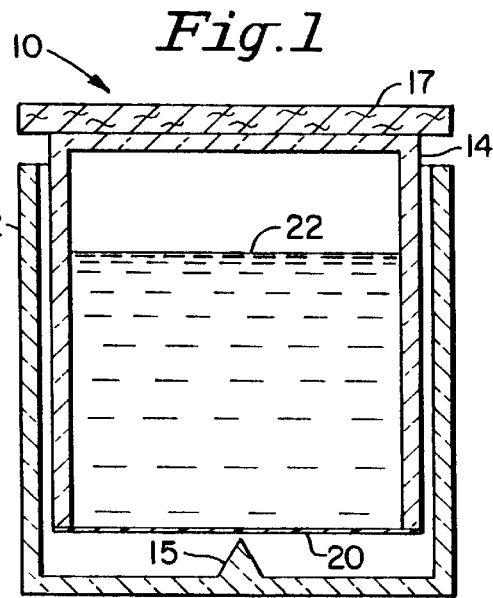
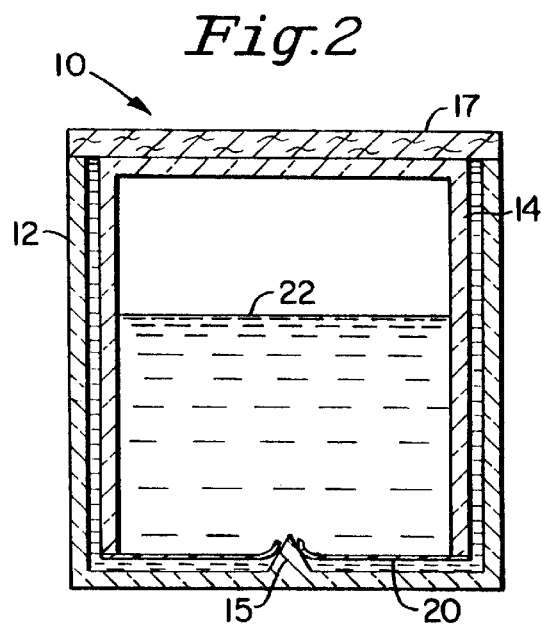
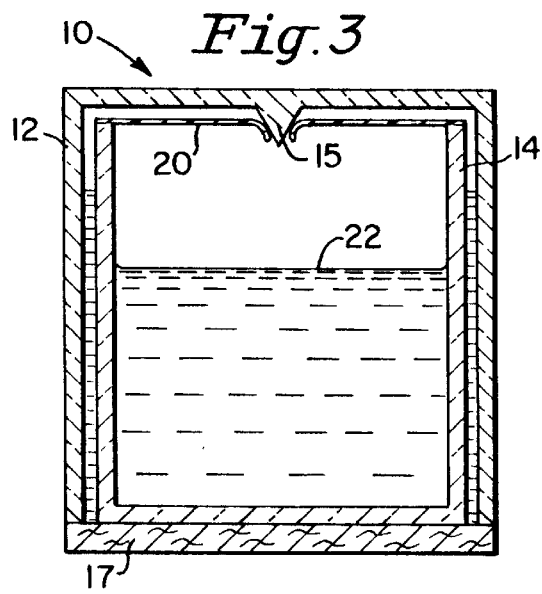
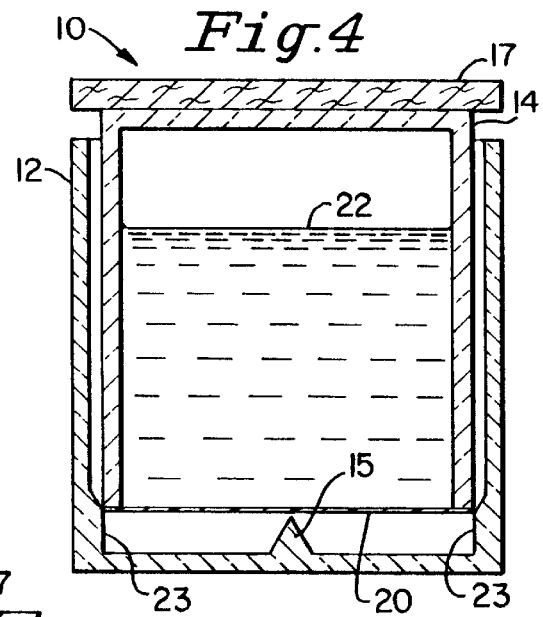
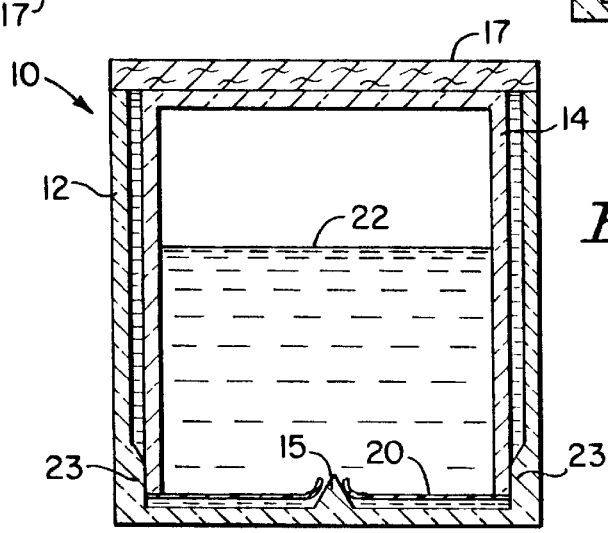

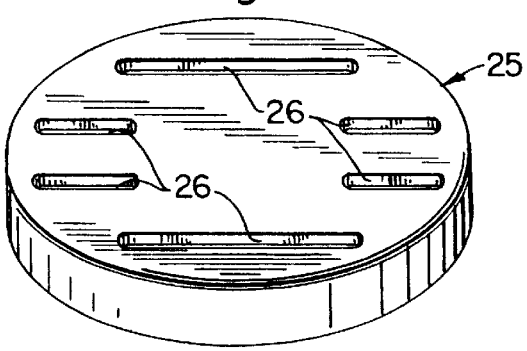
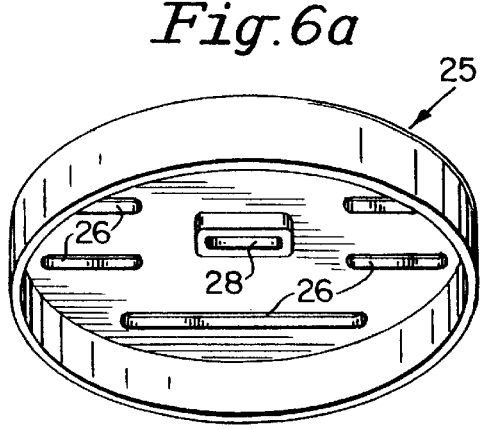
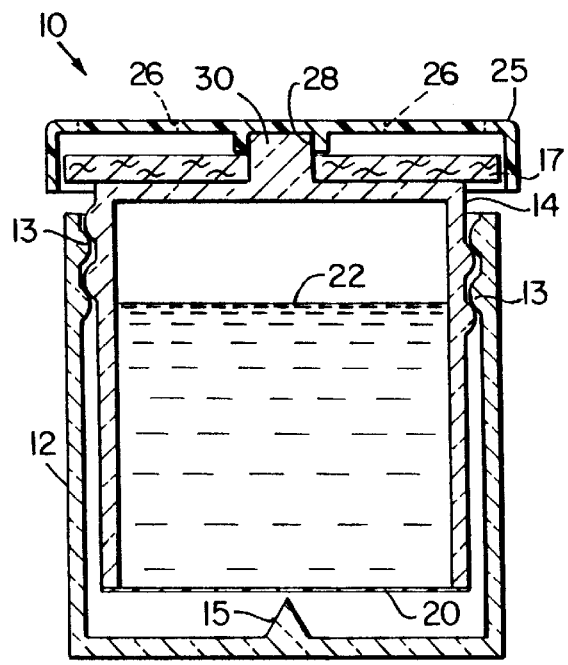
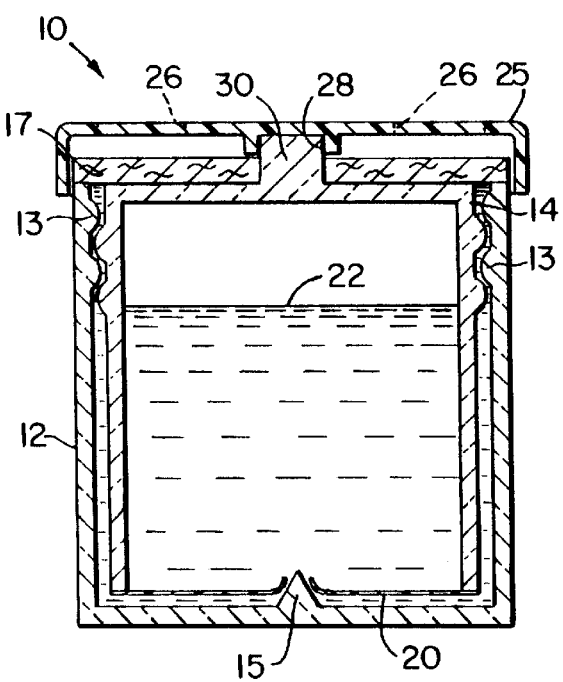

LIQUID AIR FRESHENER DISPENSER DEVICE WITH NONPOROUS CAPILLARY WICKING FUNCTION

BACKGROUND OF THE INVENTION

This invention generally relates to dispensers of vaporizable media. More specifically, this invention relates to a device for dispensing a fragrance or deodorant in the form of a vapor for air freshening in an enclosed environment.

The need for effectively combating airborne malodors in homes and enclosed public buildings, by odor masking or destruction, is well established. Various kinds of vapor-dispensing devices have been employed for this purpose. The most common of such devices is the aerosol container which propels minute droplets of an air freshener composition into the air. Another common type of dispensing device is a dish containing or supporting a body of gelatinous matter which when it dries and shrinks releases a vaporized air-treating composition into the atmosphere. Other products such as deodorant blocks are also used for dispensing air-treating vapors into the atmosphere by evaporation. Another group of vapor-dispensing devices utilizes a carrier material such as paperboard impregnated or coated with a vaporizable composition.

A number of recent developments include a liquid air-treating composition in an enclosure, all or part of which is formed of a polymeric film through which the air-treating composition can migrate to be released as a vapor at an outer surface. Use of this type of permeable polymeric membrane controls the dispensing of air-treating vapors and tends to eliminate great variations in the rate of dispensing over the life of the product.

Wicking devices are well known for dispensing volatile liquids into the atmosphere, such as fragrance, deodorant, disinfectant or insecticide active agent.

A typical wicking device utilizes a combination of a wick and emanating region to dispense a volatile liquid from a liquid reservoir. Wicking devices are described in U.S. Pat. Nos. 1,994,932; 2,597,195; 2,802,695; 2,804,291; 3,550,853; 4,286,754; 4,413,779; 4,454,987; 4,913,350; and 5,000,383; incorporated by reference.

Of special interest with respect to the present invention are wicking dispenser devices in which the wicking action is promoted by a nonporous wick structure. This type of device is described in U.S. Pat. Nos. 2,847,976; 3,283,787; 4,913,350; and 5,121,881; incorporated by reference.

Some air freshener dispensers are expensive to manufacture. Other air freshener dispensers are inexpensive to produce, but tend to have inferior construction and functionality.

There remains a need for a well-constructed air freshener dispenser device which can be mass-produced economically and which can deliver a vapor medium at a controlled uniform rate over an extended period of time.

Accordingly, it is an object of this invention to provide an improved air freshener dispenser device for delivering an odorant and/or deodorant vapor in an enclosed environment.

It is another object of this invention to provide an air freshener dispenser device with a primary structure which is a plastic assembly that can be produced economically by a thermoforming means.

It is another object of this invention to provide an air freshener dispenser device which has a novel assembly of vapor-emanating surface and liquid wicking means.

It is a another object of this invention to provide an air freshener dispenser device in which a liquid air freshener is transported from an enclosed reservoir to a vapor-emanating surface by capillary action with a nonporous wick structure.

It is a further object of this invention to provide an air freshener dispenser device which optionally is convertible between operational and nonoperational modes.

Other objects and advantages of the present invention shall become apparent from the accompanying description and drawings.

SUMMARY OF THE INVENTION

One or more objects of the present invention are accomplished by the provision of an air freshener dispenser device comprising:

(a) a first sheer wall container with an upside open end, and a downside closed end which has a sharp piercing structure extending vertically from the interior bottom surface of the said first container (b) a second sheer sidewall container which is inverted and internally-nested within the first container, with an upside closed end having an outer surface which comprises a vapor-emanating, means, and a downside closed end which comprises an impermeable membrane that is closely positioned above the interior piercing structure of the said first container, and wherein the coextensive sidewalls of the two containers are in a capillary spacing proximity; and (c) a reservoir content of liquid air freshener medium which is confined within the interior volume of the internally-nested second container;

wherein the dispenser device is in an operational mode when the second container is in an adjusted internally-nested position with the downside impermeable membrane breached by the interior piercing structure of the first container, and with the said capillary spacing proximity of the container sidewalls providing a wicking means for transport of the liquid air freshener medium, which is released from the interior reservoir through the pierced impermeable membrane and which is conducted by capillary action to the vapor-emanating surface for evaporation into the atmosphere.

DESCRIPTION OF THE DRAWINGS

FIG. 1 is a cross-sectional side view of an invention air freshener dispenser device before activation into an operational air freshener dispensing mode.

FIG. 2 is a cross-sectional side view of a FIG. 1 invention dispenser device which is in an operational air freshener dispensing mode.

FIG. 3 is a cross-sectional side view of a FIG. 2 invention dispenser device which has been converted into a nonoperational air freshener dispensing mode by physical inversion of the dispenser device.

FIG. 4 is a cross-sectional side view of an invention air freshener dispenser device before activation into an operational air freshener dispenser mode, and which features lug means to support an internally-nested liquid air freshener container.

FIG. 5 is a cross-sectional side view of a FIG. 4 invention dispenser device which is in an operational air freshener dispenser mode.

FIG. 6 is a prospective top view of an optional vented cap-type cover means for an invention air freshener dispenser device, and FIG. 6a is a prospective bottom view of the FIG. 6 cap-type cover means.

FIG. 7 is a cross-sectional side view of an invention air freshener dispenser device with a FIG. 6 cap-type cover means secured to an internally-nested liquid air freshener container.

FIG. 8 is an elevational side view of a FIG. 7 air freshener dispenser device which is in an operational air freshener dispensing mode.

DESCRIPTION OF THE PREFERRED EMBODIMENTS

FIG. 1 is a cross-sectional side view of present invention air freshener dispenser 10 which is in a non-operational mode.

Sheer wall container 12 has sharp prong 15 extending vertically from the interior bottom surface of container 12. Prong 15 is illustrated as a simple structure in a centrally disposed position. Optionally, more than one prong 15 can be provided in selected positions on the bottom surface of container 12.

Sheer wall container 14 is inverted and internally-nested within container 12. The upside closed end of container 14 is adapted to provide a vapor-emanating means. As illustrated in FIG. 1, the vapor-emanating means is liquid-permeable absorbent matrix 17.

In a further embodiment, the vapor-emanating means is structurally integrated within the outer surface of the upside closed end of container 14. This type of vapor-emanating means can be in the form of grooves or striations which can function as effective nonporous capillary conduits.

Container 14 in FIG. 1 has a downside end which is sealed by means of impermeable membrane 20. As illustrated in FIG. 1, membrane 20 is closely positioned above prong 15, and membrane 20 is susceptible to piercing by prong 15. Membrane 20 can be in the form of a flexible, semi-rigid or rigid thin film, such as aluminum foil sealed to the peripheral bottom rim of container 14.

The coextensive sidewalls of container 12 and container 14 are in a capillary spacing proximity. Container 14 has an enclosed reservoir content of liquid air freshener medium 22.

FIG. 2 is a cross-sectional side view of FIG. 1 air freshener dispenser device 10 which has been activated into an operational air freshener dispensing mode.

In dispenser device 10 of FIG. 2, membrane 20 is breached by prong 15. Liquid air freshener medium 22 passes through the pierced opening in membrane 20, and is conducted by capillary action to absorbent matrix 17, which functions as a vapor-emanating means for dispersion of air freshener medium 22 into the atmosphere.

FIG. 3 illustrates dispenser device 10 of FIG. 2 which has been oriented in an inverted stance. By inversion of dispenser device 10 as shown in FIG. 3, an operational air freshener dispensing mode is converted into a non-operational dispensing mode. Air freshener medium 22 no longer has access to pierced membrane 20 for release from the enclosed reservoir volume of container 14.

FIG. 4 is a cross-sectional side view of invention dispenser device 10 of FIG. 1 which additionally features lugs 23 that are frictional means to support container 14 and membrane 20 out of contact with prong 15. This embodiment is for the purpose of preventing inadvertent piercing of membrane 20 during assembly of dispenser device 10, or subsequently during packaging and transporting of dispenser device 10.

FIG. 5 is a cross-sectional side view of dispenser device 10 of FIG. 4 which has been converted into an operational air freshener dispensing mode by breaching of membrane 20 by prong 15. The conversion is effected by movement of container 14 frictionally along lugs 23 into the position illustrated in FIG. 5.

FIG. 6 is a prospective top view of cap cover 25, and FIG. 6a is a prospective bottom view of cap cover 25. Vents 26 in cap cover 25 are adapted to allow passage of air freshener medium 22 vapor when cap cover 25 optionally is utilized in combination with invention dispenser device 10.

Connector slot 28 in cap cover 25 of FIG. 6a serves as a means for attachment of cap cover 25 to dispenser device 10. Other structural types of attachment means may be employed.

FIG. 7 is a cross-sectional side view of invention dispenser device 10 which has cap cover 25 of FIG. 6 secured to container 14, by means of a slot 28 interlock with key 30 which is a structural extension of container 14.

FIG. 7 also illustrates thread means 13 between the coextensive sidewalls of container 12 and container 14. Thread means 13 serves to prevent accidental downward movement of container 14. Thread means 13 permits controlled downward adjustment of container 14 for activation of the air freshener dispensing mode.

Structural adaptations other than thread means 13 can be employed for control of container 14 movement. These include features such as nodes or ridges interacting between the coextensive sidewalls of container 12 and container 14 in the manner of thread means 13.

FIG. 8 is an elevational side view of dispenser device 10 of FIG. 7, in which container 14 is adjusted downward by thread means 13. Air freshener medium 22 is transported by capillary action to absorbent matrix 17 (shown in FIG. 7), and air freshener medium 22 evaporates into the atmosphere through vents 26 of cap cover 25 (shown in FIG. 6).

The capillary spacing proximity between the coextensive sidewalls of container 12 and container 14 is between about 0.1–2 millimeters, and is in an interdependent hydrodynamic relationship with the surface tension properties of liquid air freshener medium 22.

Typically, container 12 is a cylinder which has an interior diameter between about 1.5–5 centimeters, and a height between about 2–12 centimeters. The dimensions of internally-nested container 14 are adapted to conform structurally with container 12, and to provide the required capillary spacing proximity between the coextensive sidewalls of container 12 and container 14.

Container 12 and container 14 can be constructed of the same or different thermoplastic compositions. Typically, container 12 and container 14 are transparent structures which are injection or thermoform molded from a polymer such as polyethylene, polypropylene, polystyrene, polyvinyl acetate, polyamide, polymethacrylate, and the like. Container 12 and container 14 can be annular-shaped structures with vertical or slanted sidewalls, or they can be square or rectangular structures. Container 12 and container 14 can be any convenient design, with the proviso that the conformational sidewalls provide at least an effective degree of capillary spacing proximity, and internally-nested container 14 is in potential or actual interacting contact with both absorbent matrix 17 and liquid air freshener medium 22 in dispenser device 10 as illustrated in FIGS. 1–8.

Cap cover 25 as illustrated in FIG. 6 can be an injection or thermoform molded structure of a polymer such as high density polyethylene or polypropylene. Cap cover 25 also can be fabricated with a thermoset polymer such as phenol-formaldehyde resin.

The vapor-emanating surface means, such as absorbent matrix 17 in FIGS. 1–8, can be an organic or inorganic liquid-transport structure, such as a thermoplastic, thermoset, cellulosic or ceramic composition, which is secured to the outer surface of the upside end of container 14. If the vapor-emanating means is structurally integrated when the upside outer surface of container 14 (e.g., capillary-sized grooves), then the said vapor-emanating means can be formed when container 14 is molded from a thermoplastic polymer.

Air freshener medium 22 in FIGS. 1–8 can be any air treating material which can be wicked up to absorbent matrix 17 by capillary action, and dispersed into the atmosphere in vapor form. Typically air freshener medium 22 is a fragrance or a deodorant formulation in liquid form.

Air freshener medium 22 preferably is a liquid fragrance comprising one or more volatile organic compounds which are available from perfumery suppliers such as Firmenich Inc., Takasago Inc., Noville Inc., Quest Co., and Givaudan-Roure Corp.

Most conventional fragrance materials are volatile essential oils. The fragrance can be a synthetically formed material, or a naturally derived oil such as oil of Bergamot, Bitter Orange, Lemon, Mandarin, Caraway, Cedar Leaf, Clove Leaf, Cedar Wood, Geranium, Lavender, Orange, Origanum, Petitgrain, White Cedar, Patchouli, Lavandin, Neroli, Rose absolute, and the like.

A wide variety of chemicals are known for perfumery, such as aldehydes, ketones, esters, alcohols, terpenes, and the like. A fragrance can be relatively simple in composition, or can be a complex mixture of natural and synthetic chemical components.

A typical scented oil can comprise woody/earthy bases containing exotic constituents such as sandalwood oil, civet, patchouli oil, and the like. A scented oil can have a light floral fragrance, such as rose extract or violet extract. Scented oil also can be formulated to provide desirable fruity odors, such as lime, lemon or orange.

Synthetic types of fragrance compositions either alone or in combination with natural oils are described in U.S. Pat. Nos. 4,314,915; 4,411,829; and 4,434,306; incorporated herein by reference. Other artificial liquid fragrances include geraniol, geranyl acetate, eugenol, isoeugenol, linalool, linalyl acetate, phenethyl alcohol, methyl ethyl ketone, methylionone, isobornyl acetate, and the like.

Air freshener medium 22 also can be a liquid formulation containing a volatile pesticide such as p-dichlorobenzene, or a therapeutic agent such as menthol.

Air freshener dispenser device 10 preferably is constructed of transparent or translucent materials, such that air freshener medium 22 is visible during usage for an indication of the liquid level in the interior reservoir of container 14.

A present invention air freshener dispenser device can be produced in high volume from relatively inexpensive plastic materials. After usage, the device qualifies for disposal as a non-hazardous solid waste.

What is claimed is:

1. An air freshener dispenser device comprising:

(a) a first sheer wall container with an upside open end, and a downside closed end which has a sharp piercing structure extending vertically from the interior bottom surface of the said first container;

(b) a second sheer sidewall container which is inverted and internally-nested within the first container, with an upside closed end having an outer surface which comprises a vapor-emanating means, and a downside closed end which comprises an impermeable membrane that is closely positioned above the interior piercing structure of the said first container, and wherein the coextensive sidewalls of the two containers are in a capillary spacing proximity; and (c) a reservoir content of liquid air freshener medium which is confined within the interior volume of the internally-nested second container;

wherein the dispenser device is in an operational mode when the second container is in an adjusted internally-nested position with the downside impermeable membrane breached by the interior piercing structure of the first container, and with the said capillary spacing proximity of the container sidewalls providing a wicking means for transport of the liquid air freshener medium, which is released from the interior reservoir through the pierced impermeable membrane and which is conducted by capillary action to the vapor-emanating surface for evaporation into the atmosphere.

2. A dispenser device in accordance with claim 1 wherein the nested containers have conformational annular-shaped structures comprising a transparent thermoplastic composition.

3. A dispenser device in accordance with claim 1 wherein the vapor-emanating surface means is an absorbent matrix comprising a liquid-permeable thermoplastic, thermoset, cellulosic or ceramic composition.

4. A dispenser device in accordance with claim 1 wherein the air freshener medium is a liquid fragrance composition.

5. A dispenser device in accordance with claim 1 wherein the air freshener medium is a liquid pesticide composition.

6. A dispenser device in accordance with claim 1 wherein the air freshener medium is a liquid therapeutic composition.

7. A dispenser device in accordance with claim 1 wherein the upside closed end of the second container is structurally adapted to receive and secure a vented cap-type cover means.

8. A dispenser device in accordance with claim 1 wherein the downside impermeable membrane of the second container is supported above the piercing means by prop means.

9. A dispenser device in accordance with claim 1 wherein the internally-nested second container is adapted for adjustment by thread-type means between the sidewalls of the first and second containers.

10. A dispenser device in accordance with claim 1 wherein an operational mode is converted into a non-operational mode by inversion of the dispenser device stance.

* * * * *